United States Patent
Endries et al.

(10) Patent No.: US 6,643,605 B1
(45) Date of Patent: Nov. 4, 2003

(54) METHOD AND DEVICE FOR DETERMINING THE ENTHALPY OF WET STEAM

(75) Inventors: Hans-Joachim Endries, Essen (DE); Helmut Herbig, Mülheim (DE); Hans-Bernd Krämer, deceased, late of Vorra (DE), by Vera Krämer, widow and heir

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/535,649

(22) Filed: Mar. 24, 2000

Related U.S. Application Data

(63) Continuation of application No. PCT/DE98/02791, filed on Sep. 18, 1998.

(30) Foreign Application Priority Data

Sep. 24, 1997 (DE) .......................... 197 42 138

(51) Int. Cl.⁷ .......................... G01K 11/30; G06F 15/00
(52) U.S. Cl. .................................................. 702/136
(58) Field of Search .................. 702/136, 34, 182; 73/25.04, 24.04, 61.43, 61.44; 376/256, 248, 317, 352; 60/39, 182, 644.1, 655, 775, 39.5, 673; 374/35

(56) References Cited

U.S. PATENT DOCUMENTS

| | | | | |
|---|---|---|---|---|
| 3,596,516 A | * | 8/1971 | Haynes, Jr. .................... 374/42 |
| 3,873,817 A | * | 3/1975 | Liang .......................... 700/287 |
| 4,149,403 A | * | 4/1979 | Muldary et al. ........... 73/29.03 |
| 4,396,063 A | * | 8/1983 | Godbey ................. 166/250.06 |
| 4,681,466 A | | 7/1987 | Chien |
| 4,753,106 A | * | 6/1988 | Brenner et al. |
| 4,769,593 A | * | 9/1988 | Reed et al. .................. 324/668 |
| 4,833,688 A | * | 5/1989 | Smith ........................... 374/42 |
| 4,836,032 A | | 6/1989 | Redus |
| 4,932,788 A | * | 6/1990 | Yeh .............................. 374/35 |
| 5,061,431 A | * | 10/1991 | Silvestri, Jr. ................. 376/252 |
| 5,526,386 A | * | 6/1996 | Tsiklauri et al. ............. 376/317 |
| 5,559,691 A | * | 9/1996 | Monta et al. ................. 700/83 |
| 5,793,831 A | * | 8/1998 | Tsiklauri et al. ............. 376/317 |
| 5,970,702 A | * | 10/1999 | Beichel ........................ 60/775 |

FOREIGN PATENT DOCUMENTS

| | | |
|---|---|---|
| CH | 434 798 | 10/1967 |
| DE | 1 046 068 | 12/1958 |
| JP | 57-120839 | 7/1982 |

OTHER PUBLICATIONS

"Messung der Dampfnässe" (Verein Deutscher Igneneure), dated Jul. 1979, VDI Handbuch Energietechnik 1, pp. 1–11, pertains to the wetness–determination of steam, as mentioned on p. 3 of the specification.

* cited by examiner

Primary Examiner—John Barlow
Assistant Examiner—Demetrius Pretlow
(74) Attorney, Agent, or Firm—Laurence A. Greenberg; Werner H. Stemer; Ralph E. Locher

(57) ABSTRACT

A method and a device for determining an enthalpy of wet steam, in particular of wet steam at an outlet of a steam turbine. A part volume flow of the wet steam is mixed with a reference gas to form a mixture, so that the liquid constituents of the part volume flow evaporate completely. An enthalpy of the reference gas and an enthalpy of the mixture is then determined by measured physical variables and an enthalpy of the wet steam is calculated from these enthalpies.

10 Claims, 1 Drawing Sheet

METHOD AND DEVICE FOR DETERMINING THE ENTHALPY OF WET STEAM

CROSS-REFERENCE TO RELATED APPLICATION

This is a continuation of copending International Application PCT/DE98/02791, filed Sep. 18, 1998, which designated the United States.

BACKGROUND OF THE INVENTION

FIELD OF THE INVENTION

The invention relates to a method and a device for determining an enthalpy of wet steam, in particular of wet steam at an outlet of a steam turbine. The invention relates specifically to steam power processes for current generation in nuclear power stations, in which the turbine operates in a wet-steam zone.

Methods for determining the enthalpy of hot steam, that is to say of superheated steam, are known, for example, from Published, Non-Prosecuted German Patent Application DE 10 46 068 A. The reference describes a method for improving intermediate superheating and feed-water preheating in steam power plants, particularly those with an output of heating or manufacturing steam. The steam being divided, after expansion in a high-pressure machine, into two part steam quantities, only one part of which is led through an intermediate superheater, and both part quantities expanding separately from one another to the same outlet pressure in a double-flow medium-pressure machine and thereafter being combined again downstream of the machine. A definite mixture temperature is established according to the quantity ratio and the temperatures of the part steam quantities. The method for determining the enthalpy of hot steam at the outlet of steam turbines, in which the pressure and temperature of the hot steam are measured and the enthalpy is calculated from them, is unsuitable for determining the enthalpy of wet steam, since pressure and temperature, as state variables, are coupled in the wet-steam zone, that is to say they are not independent of one another. A state of a point in the wet-steam zone is completely fixed only when the quantity ratio of the two gaseous and liquid phases is also known. This presents considerable difficulties, in practice, since the liquid constituents are generally not distributed uniformly in the wet steam. The German Patent Application DE 10 46 068 A is therefore concerned with a method and a device for regulating steam power plants. The steam, after expanding in the high-pressure machine, is divided as a whole into two part steam quantities that are combined (mixed) again later downstream of the machine. A definite mixture temperature being capable of being established according to the quantity ratio and the temperatures of the part steam quantities.

Various measuring methods for measuring steam wetness, which are known from the literature and from use in the power station sector, are presented in the Directive VDI 2043 "Messung der Dampfnässe" ["Measurement of Steam Wetness"], Jul. 7, 1979. The VDI Directive is concerned with various methods for measuring steam wetness which are known from the literature and from use in the power station sector. According to Chapter 3.4., titled " Überhitzungskalorimeter" [Superheating Calorimeter], it is proposed, in order to determine steam wetness, to superheat a wet-steam sample by a supply of energy. The state of the superheated steam is determined by measuring the pressure and temperature. The heat flow supplied is likewise measured.

SUMMARY OF THE INVENTION

It is accordingly an object of the invention to provide a method and a device for determining the enthalpy of wet steam which overcome the above-mentioned disadvantages of the prior art methods and devices of this general type, which method is simple in measurement terms.

With the foregoing and other objects in view there is provided, in accordance with the invention, a measurement and calculation method for determining an enthalpy of steam, which includes: mixing, for sampling purposes, a part volume flow of wet steam with a reference gas such that liquid constituents of the part volume flow evaporate completely and results in a mixture formed from the reference gas and the part volume of the wet steam;

determining an enthalpy of the reference gas and an enthalpy of the mixture from measured physical variables; and calculating an enthalpy of the wet steam from the enthalpy of the reference gas and the enthalpy of the mixture.

In the measurement and calculation method for determining the enthalpy of wet steam, in particular of wet steam at the outlet of a steam turbine, for sampling purposes a part volume flow of the wet steam is mixed with a reference gas to form a mix, such that the liquid constituents of the part volume flow evaporate completely. The enthalpy of the reference gas and the enthalpy of the mixture are then determined by measured physical variables, and the enthalpy of the wet steam being calculated from these enthalpies. One advantage of the method is that it thereby becomes possible to determine the steam content from the pressure and enthalpy of the wet steam.

In this case, preferably, only a part volume flow of hot steam is sampled as the reference gas from the steam flow. The hot steam is supplied as the reference gas to a mixing space, in such a way that, when it is mixed with a further part volume flow of the wet steam, the liquid constituents contained therein evaporate completely. As a result, two variables are known by measurements, namely the enthalpy of the reference gas or, according to the preferred development of the invention, of the hot steam and the enthalpy of a reference-gas/wet-steam mixture, by use of which enthalpies the variable required, namely the enthalpy of the wet steam, can be calculated.

In a development of the method, the part volume flow of the wet steam is mixed essentially adiabatically with the reference gas. There is therefore no need to take into account a change in enthalpy during the mixing operation.

In a preferred development, the reference gas is hot steam. The wet steam and the hot steam form a mixture, the state point of which is located in the hot-steam zone. Known methods may subsequently be employed in order to determine the enthalpy of the mixture. The embodiments which are illustrated below employ the terms "mix" and "mixture" according to the use of a flow having two or more components, in the first case, and according to a single-component fluid, in the second case. The single-component fluid and the multi-component fluid may be single-phase or two-phase. The two terms are to be considered as synonyms within the scope of the invention.

In an advantageous refinement of the method, a pressure and/or a temperature and/or a quantity of the reference gas are regulated as a function of the relative humidity of the mixture. In this refinement, the properties of the reference gas can be set in such a way that the liquid constituents of the wet-steam part reliably evaporate completely when the properties of the wet steam change over the course of time.

According to a preferred development in which hot steam is used as the reference gas, the pressure and/or the temperature and/or the quantity of the hot steam are regulated as a function of the distance of a state point of the mixture in the hot-steam zone from the saturation line.

It is necessary, furthermore, to determine the enthalpy of the reference gas and/or of the mixture in each case by measuring the pressure and the temperature. The enthalpy can be calculated directly in a known way from these state variables and from the quantity of the reference gas or of the mix.

Particularly when there are continuous streams of the reference gas and the wet steam, it is advantageous if the wet-steam part and the reference gas are introduced into a mixing stage and the enthalpy of the mixture is determined at the end of the mixing stage. Along the way through the mixing stage, the liquid constituents can evaporate completely and a homogeneous pressure and homogeneous temperature can be established in the mixture.

In a development of the method, the enthalpy of the wet steam is calculated continuously or quasi-continuously, taking into account the mass flows of the wet-steam part and of the reference gas. This affords the possibility of continuously monitoring important variables of the steam power process and, where appropriate, of readjusting the steam power process. A development is preferred, in which the mass flows of the mixture and of the reference gas are measured. In the case of stationary flows, the mass flow of the wet-steam part can then be calculated.

In yet another development of the method according to the invention, the efficiency of the steam turbine is determined from the enthalpy of the wet steam.

A device according to the invention for carrying out the method has a first supply for supplying the wet steam and a second supply for supplying the reference gas. Both supplies open into a mixing space, and, the device furthermore, has a measuring device for determining the enthalpy of the mixture in the mixing space. A development is preferred, in which the two supplies open into the mixing space via a common nozzle. In this case, the wet steam and the reference gas, in particular the hot steam, can be combined in the manner of a sample mixture. It is preferred, furthermore, that the nozzle have an inner outlet orifice which is surrounded by an outer outlet orifice, one of the supplies opening into the mixing space at the inner outlet orifice and the other supply at the outer outlet orifice.

Other features which are considered as characteristic for the invention are set forth in the appended claims.

Although the invention is illustrated and described herein as embodied in a method and a device for determining the enthalpy of wet steam, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
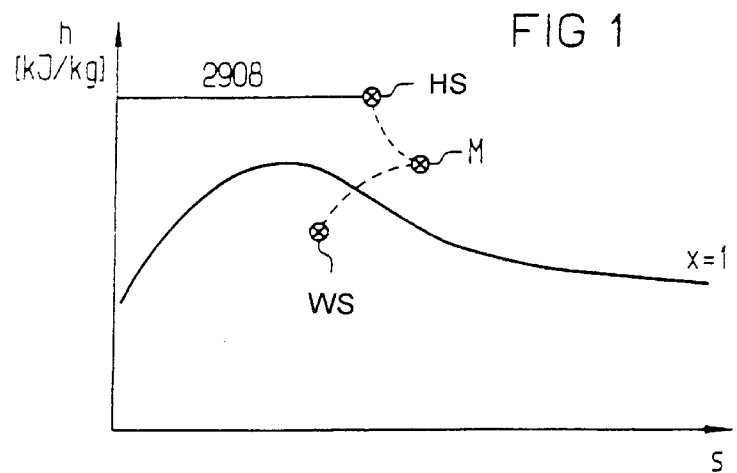
FIG. 1 is an h-s graph.

In all the figures of the drawing, sub-features and integral parts that correspond to one another bear the same reference symbol in each case. Referring now to the figures of the drawing in detail and first, particularly, to FIG. 1 thereof, there is shown a graph, in which a specific enthalpy h is plotted against a specific entropy s of steam. A continuous line marks a boundary between a hot-steam zone (above the line) and a wet-steam zone (below the line). The graph indicates states of a hot steam HS, a wet steam WS and a resulting mixture M produced by mixing the hot steam HS and a part of the wet steam WS. The intermixing process proceeds, as indicated by the broken lines. For the hot steam HS there is a source which makes it possible to extract hot steam having a pressure p=12 bar, at a temperature of q=240° C., with a mass flow of 2 kg/s. These variables are kept approximately constant. In a variant of the method, the hot-steam source becomes variable, that is to say it is set as a function of a distance of a state point of the mixture M from a saturation line. A specific enthalpy of approximately 2908 kJ/kg corresponds to the variables, namely the pressure p=12 bar and the temperature q=240° C. This is approximately the state of an intermediately superheated hot steam during processes with saturated-steam turbines.

Figure 2:
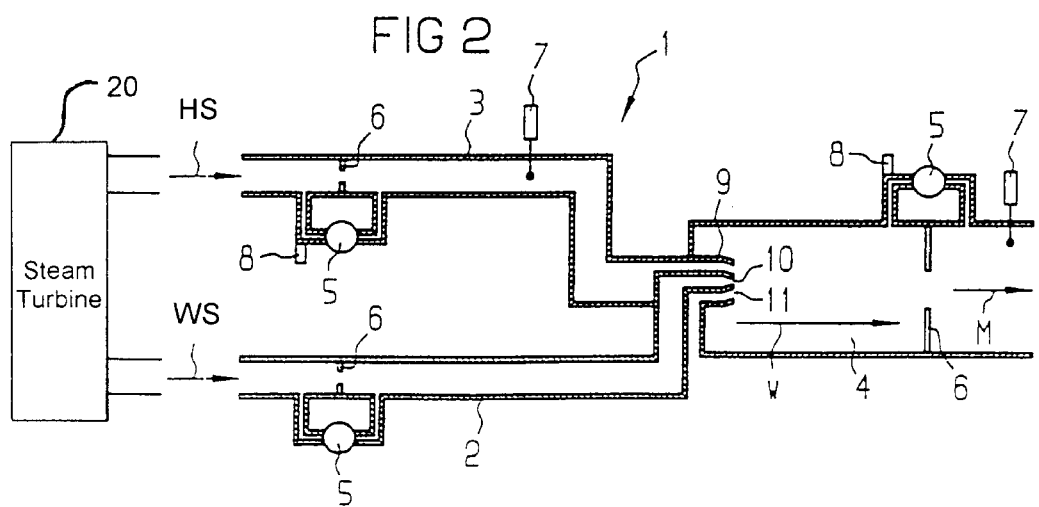
FIG. 2 is a diagrammatic, sectional view of an embodiment of a device according to the invention.

FIG. 2 illustrates a device 1 for carrying out the method for determining the enthalpy of the wet steam WS. Part of the wet steam WS (a wet-steam sample) is led into a mixing space 4 through a first supply line 2 and the hot steam HS (reference-gas sample) is led into the mixing space 4 through a second supply line 3. Sampling of the wet steam WS from the entire stream of the wet steam WS passing through a steam turbine 20 thus takes place. The supply line 2 opens into the mixing space 4 at an inner outlet orifice 10 of a double-flow nozzle 9. The second supply line 3 opens out at an outer outlet orifice 11 that surrounds the inner outlet orifice 10 in a continuously closed manner. The liquid constituents of the wet-steam part WS evaporate over a mixing stage w and the state variables of the two steams WS, HS supplied by the two supply lines 2, 3 are assimilated into one another. At an end of the mixing stage w, the pressure p and the temperature q as well as a mass flow m of the mixture are measured or determined. For this purpose, a differential-pressure meter 5, a temperature sensor 7 and an absolute-pressure meter 8 are located there. The differential-pressure meter 5 measures the pressure drop between two points along the flow, upstream and downstream of a throttle, for example a diaphragm 6. The mass flow mM of a mixture M is calculated from the pressure difference, using Bernoulli's equation. A specific enthalpy hM of the mixture M is calculated in a known way from the pressure and temperature of the mixture M. The mass flow mHS and a specific enthalpy hHS of the hot steam HS are determined in a similar way in the second supply line 3. The measuring instruments are disposed expediently, that is to say according to the possibilities available on the spot. The measuring instruments are particularly preferably disposed in the light of and in accordance with technical directives and standards, adherence to the standard DIN EN ISO 5167-1, titled "Durchflußmessung von Fluiden mit Drosselgeräten" [Measurement of Fluid Flow by Means of Pressure Differential Devices], November 1995, is essential for the accuracy of the method described in FIG. 2.

As regards the first supply line 2, the mass flow mWS of the wet-steam part WS is determined from the difference mM−mHS. The measuring instruments illustrated in the first supply line 2 serve, above all, for checking purposes and, if appropriate, could even be dispensed with. The use of a mass-flow meter, capable of measuring wet-steam flows in lines of small diameter, would prove advantageous. The meter makes it possible to increase the accuracy of the entire method even further. An evaluation device, not shown, records the measured values, calculates the intermediate variables from these and additionally calculates the target variable, namely the specific enthalpy hWS of the wet steam WS, according to the equation $$h_{WS} = h_M - \frac{m_{HS}}{m_{WS}} \cdot (h_{HS} - h_M)$$

It is essential, for reliable determination of the specific enthalpy hWS, to divert a part flow of the wet steam WS having physical properties representative of the entire flow. For this purpose, it is proposed to use, here, a device for homogenizing the physical properties of the flow and to have an extraction point that is disposed directly downstream of the homogenizing device. As regards the configuration of the extraction point, reference is made and attention drawn in full to the Directive VDI 2043 already mentioned above.

The supply lines 2, 3 and the mixing space 4 are well insulated thermally relative to the outside, so that, at most, insignificant heat transfer takes place between the steam and the surroundings, at least in the region between the measuring instruments 5, 6, 7, 8 in the supply lines 2, 3 and the mixing space 4.

The double-flow nozzle 9, through which the steams WS, HS are introduced into the mixing space 4, causes expansion, so that the pressure of the mixture M is at least lower than the pressure of the steam HS, WS having the higher pressure. The double-flow nozzle 9 ensures good intermixing of the two steams HS, WS, with the result that a short mixing stage w can be selected. It also ensures that the mixing process proceeds at least approximately adiabatically. In contrast to what is illustrated in FIG. 2 for reasons related to the drawing, for the same reason the measuring instruments 5, 6, 7, 8 in the two supply lines 2, 3 are located immediately upstream of the double-flow nozzle 9.

The invention makes it possible to determine the enthalpy of the wet steam WS, in particular of the wet steam WS at the outlet of a steam turbine in the steam power process of a nuclear power station. By using a hot-steam source, the difficulties in determining the steam content are avoided and known measurement methods can be employed. The method according to the invention can therefore be carried out cost-effectively.

We claim:

1. A measurement and calculation method for determining an enthalpy of a wet steam, which comprises:
    mixing, for sampling purposes, a part volume flow of the wet steam with hot steam causing liquid constituents of the part volume flow to evaporate completely and resulting in a mixture formed from the hot steam and the part volume of the wet steam;
    determining an enthalpy of the hot steam and an enthalpy of the mixture from measured physical variables; and
    calculating an enthalpy of the wet steam from the enthalpy of the hot steam and the enthalpy of the mixture.

2. The method according to claim 1, which comprises mixing the part volume flow of the wet steam substantially adiabatically with the reference gas.

3. A measurement and calculation method for determining an enthalpy of a wet steam, which comprises:
    mixing, for sampling purposes, a part volume flow of the wet steam with a reference gas causing liquid constituents of the part volume to flow evaporate completely and resulting in a mixture formed from the reference gas and the part volume of the wet steam;
    regulating at least one of a pressure, a temperature and a quantity of the reference gas in dependence on at least one of a relative humidity and a position of a state point of the mixture;
    determining an enthalpy of the reference gas and an enthalpy of the mixture from measured physical variables; and
    calculating an enthalpy of the wet steam from the enthalpy of the reference gas and the enthalpy of the mixture.

4. The method according to claim 3, which comprises determining the enthalpy of the reference gas and the enthalpy of the mixture in each case by measuring a pressure and a temperature.

5. A measurement and calculation method for determining an enthalpy of a wet steam, which comprises;
    introducing the wet steam and a reference gas into a mixing stage;
    mixing, for sampling purposes, a part volume flow of the wet steam with the reference gas causing liquid constituents of the part volume flow to evaporate completely and resulting in a mixture formed from the reference gas and the part volume of the wet steam;
    determining an enthalpy of the reference gas and an enthalpy of the mixture from measured physical variables, determining the enthalpy of the mixture at an end of the mixing stage; and
    calculating an enthalpy of the wet steam from the enthalpy of the reference gas and the enthalpy of the mixture.

6. A measurement and calculation method for determining an enthalpy of a wet steam, which comprises:
    mixing, for sampling purposes, a part volume flow of the wet steam with the reference gas causing liquid constituents of the part volume flow evaporating completely and resulting in a mixture formed from the reference gas and the part volume of the wet steam;
    determining an enthalpy of the reference gas and an enthalpy of the mixture from measured physical variables;
    calculating an enthalpy of the wet steam from the enthalpy of the reference gas and the enthalpy of the mixture; and
    calculating the enthalpy of the wet steam continuously, taking into account a mass flow of the wet steam and of the reference gas.

7. A measurement and calculation method for determining an enthalpy of a wet steam, which comprises:
    mixing, for sampling purposes, a part volume flow of the wet steam with the reference gas causing liquid constituents of the part volume flow to evaporate completely and resulting in a mixture formed from the reference gas and the part volume of the wet steam;
    determining an enthalpy of the reference gas and an enthalpy of the mixture from measured physical variables;
    calculating an enthalpy of the wet steam from the enthalpy of the reference gas and the enthalpy of the mixture; and calculating the enthalpy of the wet steam quasi-continuously, taking into account a mass flow of the wet steam and of the reference gas.

8. The method according to claim 7, which comprises measuring a mass flow of the mixture and the mass flow of the reference gas.

9. A measurement and calculation method for determining an enthalpy of a wet steam at an outlet of a steam turbine, which comprises:

mixing, for sampling purposes, a part volume flow of the wet steam with hot steam causing liquid constituents of the part volume flow to evaporate completely and resulting in a mixture formed from the hot steam and the part volume of the wet steam;

determining an enthalpy of the hot steam and an enthalpy of the mixture from measured physical variables; and calculating an enthalpy of the wet steam from the enthalpy of the hot steam and the enthalpy of the mixture.

10. The method according to claim 9, which comprises determining an efficiency of the steam turbine from the enthalpy of the wet steam.

* * * * *